United States Patent [19]

Rise et al.

[11] Patent Number: 4,690,144

[45] Date of Patent: Sep. 1, 1987

[54] WIRELESS TRANSCUTANEOUS ELECTRICAL TISSUE STIMULATOR

[75] Inventors: Mark T. Rise, Minneapolis; David J. Stanton, Anoka, both of Minn.

[73] Assignee: Medtronic, Inc., Minneapolis, Minn.

[21] Appl. No.: 364,660

[22] Filed: Apr. 2, 1982

[51] Int. Cl.[4] .............................................. A61N 1/36
[52] U.S. Cl. ............................................... 128/419 R
[58] Field of Search ............ 128/419 R, 419 PG, 421, 128/22, 23, 798; 340/696

[56] References Cited

U.S. PATENT DOCUMENTS

| | | | |
|---|---|---|---|
| 2,047,308 | 7/1936 | Chapman | 128/798 |
| 3,587,561 | 6/1971 | Ziedonis | 128/662 |
| 4,066,086 | 1/1978 | Alferness et al. | 128/421 |
| 4,072,898 | 2/1978 | Hellman et al. | 340/696 |
| 4,121,594 | 10/1978 | Miller et al. | 128/422 |
| 4,147,171 | 4/1979 | Greene et al. | 128/421 |
| 4,158,812 | 6/1979 | Hellman et al. | 340/696 |
| 4,241,331 | 12/1980 | Taeuber et al. | 340/696 |
| 4,257,423 | 3/1981 | McDonald et al. | 128/419 PG |

FOREIGN PATENT DOCUMENTS 0027363 10/1980 European Pat. Off. .

OTHER PUBLICATIONS

Dow Corning Wright, advertisement for transcutaneous electrical neuro-stimulator.

Primary Examiner—William E. Kamm
Attorney, Agent, or Firm—Merchant, Gould, Smith, Edell, Welter & Schmidt

[57] ABSTRACT

A transcutaneous electrical tissue stimulator comprises an electrical tissue stimulation generator (10, 41) attachable to the human body and a remote controller (37, 40) therefor. Generator (10) includes a plurality of rigid printed circuit boards (73-75) having components (91, 92) mounted thereon, each circuit board (73-75) interconnected with flexible printed circuit board (76, 77) and terminal means (51-54) for delivery of electrical tissue stimulation to electrodes (12-15). Remote programmer (37, 40) comprises user controls (39) for control of generator (10, 41) stimulation mode or parameters via telemetric link (42d, 42a).

9 Claims, 9 Drawing Figures

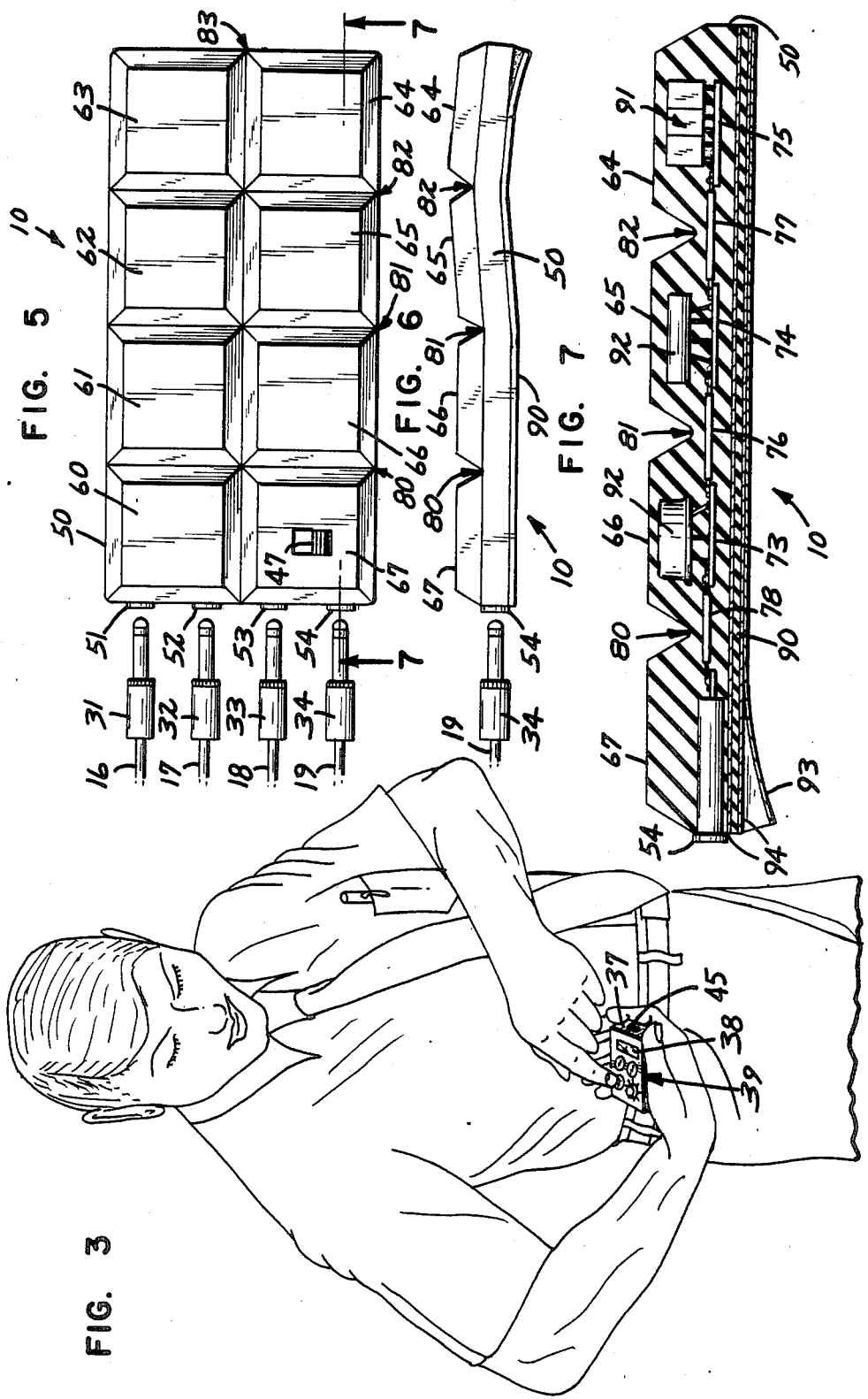

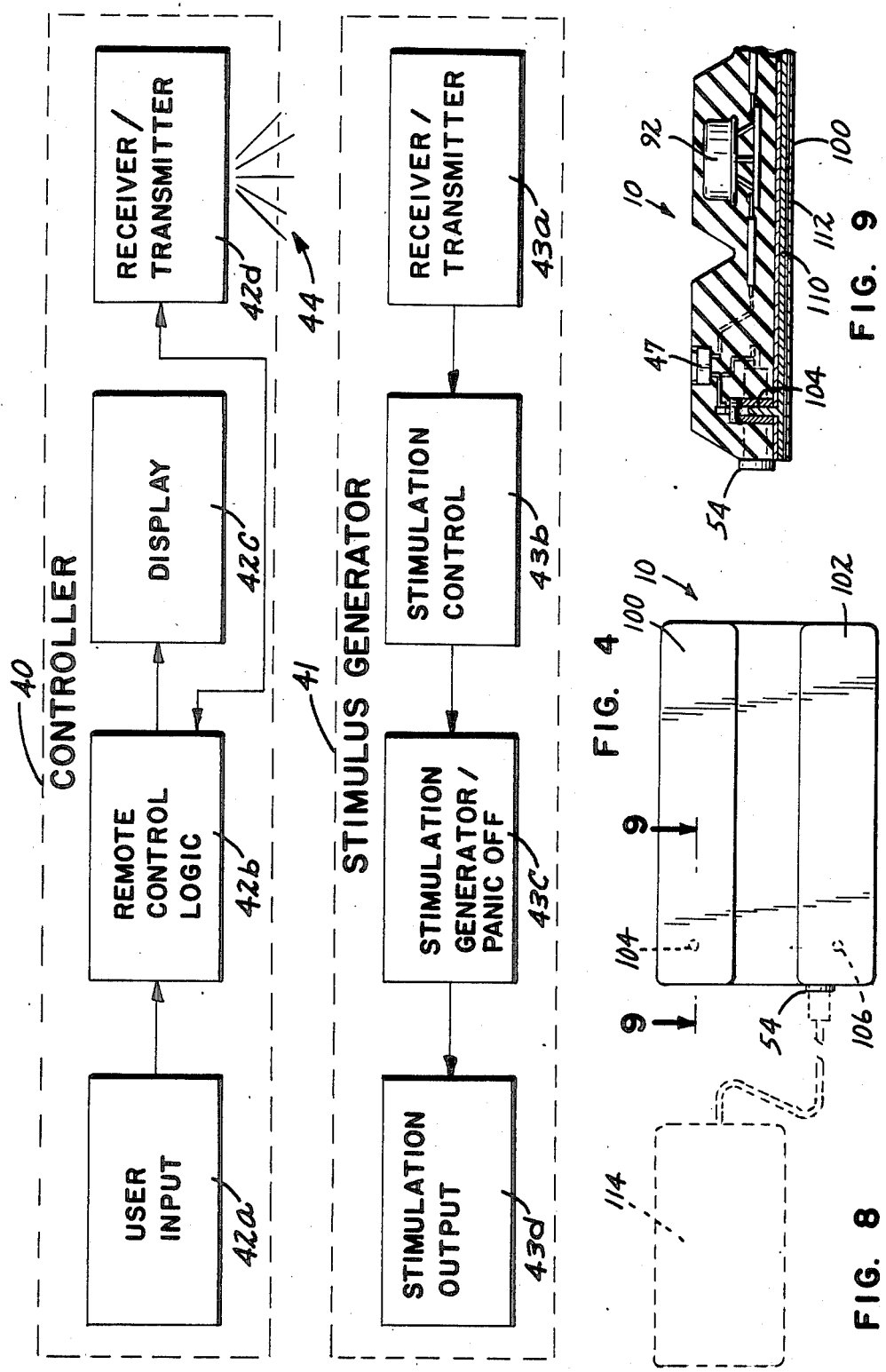

WIRELESS TRANSCUTANEOUS ELECTRICAL TISSUE STIMULATOR

FIELD OF THE INVENTION

This invention pertains to the field of tissue stimulators used in the field of medicine for the relief of pain, muscle stimulation, etc. More particularly, the invention relates to an improved transcutaneous electrical tissue stimulator, that eliminates heretofore necessary through-the-clothing wired-connections between the site of the stimulating electrodes and the controlling unit.

BACKGROUND OF THE INVENTION

Electrical tissue stimulators have been widely accepted as effective means for alleviating both acute and chronic pain. Other well known uses include stimulation ob bone, muscle or bladder tissues etc... Such devices generally include means for producing electric pulses and means for delivering the pulses to the desired body area. In the case of pain control, electrical stimulating pulses produce the effect of masking the sensation of pain. this method of pain control is preferrable to drug therepy for many types of pain because it avoids subjecting the patient to possible dangerous side effects.

Transcutaneous electrical tissue stimulators are one type of tissue stimulator. Generally, they comprise circuitry for generating electrical pulses, electrodes for attachment to the skin, and electrode leads for delivering the pulses to the electrodes. State of the art devices usually provide adjustments or controls for varying the stimulation produced by the device so that maximum efficacy in meeting the particular needs of each patient may be achieved. Transcutaneous stimulators are worn or carried outside the body and have electrodes secured to the skin over the affected area to apply the electrical stimulation thereto. Such systems heretofore have required the patient to run leads from the electrodes attached to the skin through his or her clothing to the location of the controller-generator unit. For many, the wires are a major drawback because they are awkward, bothersome, and unavoidably conspicuous. The result is that many patients discontinue the successful use of transcutaneous electrical tissue stimulation and select an alternative method of pain control such as drug therapy.

The present invention overcomes these problems by providing a wireless transcutaneous electrical tissue stimulator which can provide stimulation for the patient without all the attendant irritations and gadgetry of present systems.

SUMMARY OF THE INVENTION

The present invention provides an electrical tissue stimulator which does not require through-the-clothing wires. The stimulator includes an electrical stimulation generator mounted in a low profile housing and a remote programming unit for controlling the electrical stimulation generator through a telemetric link. The electrical stimulation generator includes output terminals for delivery of electrical stimulator to electrodes, circuitry for retaining received telemetric data for use in determining its mde of operation and a power source for the circuitry.

Preferrably, the electrical stimulation generator housing comprises a plurality of rigid rectangular modules flexibly connected to be conformable to the contours of the human body. Each rectangular module may include a rigid printed circuit board having electrical components mounted thereon, with each rigid circuit board connected to the adjacent board with flexible printed circuit cards providing circuit paths therebetween.

According to one aspect of the invention, the remote controlling unit may includee a plurality of analog controls and indicator lights, a keypad and liquid crystal display or any combination thereof to provide control over stimulation of modes and parameters. In the case of a liquid crystal display, full alpha-numeric message capability is possible using scrolling or other display techniques. Preferably, both the generator and a controller unit include a panic-off switch.

According to still another aspect of the invention, the electrical stimulation generator may provide for mounting one or more electrodes on the underside so that electrical tissue stimulation may be delivered to body tissue underneath the generator when attached to the body.

BRIEF DESCRIPTION OF THE DRAWING

In the drawing

FIG. 3 shows an exemplary embodiment of the remote control programmer in operation according to the present invention;

FIG. 4 is a block diagram of the remote control and generator electronics according to the present invention;

FIG. 5 shows a top view of an exemplary embodiment of the stimulus generator housing according to the present invention;

FIG. 6 shows a side view of an exemplary embodiment of the stimulus generator housing according to the present invention;

FIG. 7 shows a cut-away side view of the stimulus generator housing according to the present invention;

FIG. 8 shows a bottom view of the stimulus generator housing and electrodes according to an alternative embodiment of the present invention; and FIG. 9 shows a cut-away side view along the line 9—9 in FIG. 8.

DETAILED DESCRIPTION OF THE PREFERRED EMBODIMENT

Figure 1:
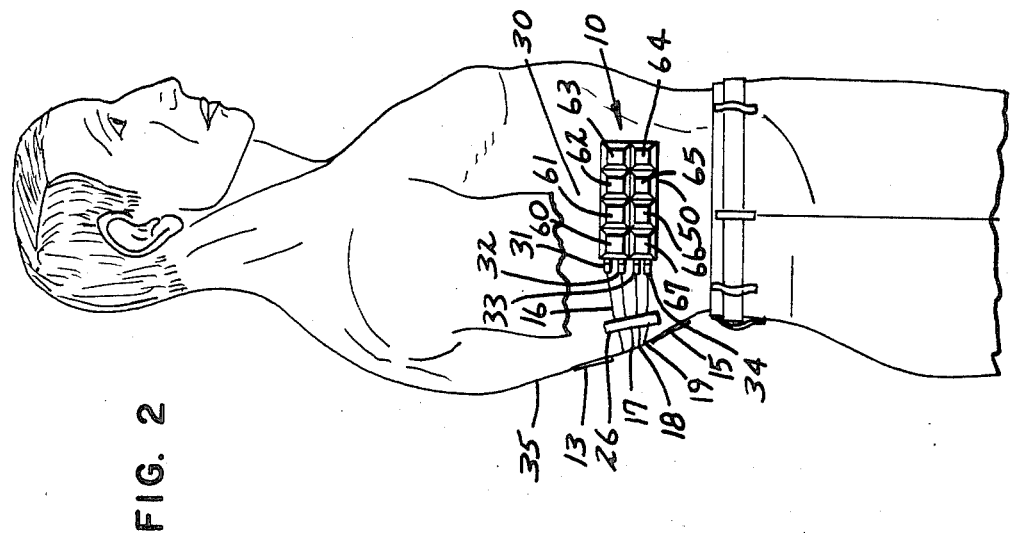
FIG. 1 shows an exemplary embodiment of the stimulus generator and electrodes attached to a human body according to the present invention.

FIG. 1 shows stimulus generator 10 adhesively or otherwise attached to the side of a patient and connected to electrodes 12, 13, 14 and 15 through the respective leads 17, 16, 18 and 19. Tape 25 and 26 secures leads 16–19 to the back 35 of the patient. Stimulation generator 10 produces electrical tissue stimulus, which comprises biphasic current in the preferred embodiment. It shall be understood that while biphasic current is preferred, any type of electrical tissue stimulation, such as DC for example, may be utilized without departing from the spirit and scope of the present invention. In another embodiment, electrodes may be provided on the underside of generator 10 and the generator 10 attached to the body over the area desired to be stimulated.

Figure 2:
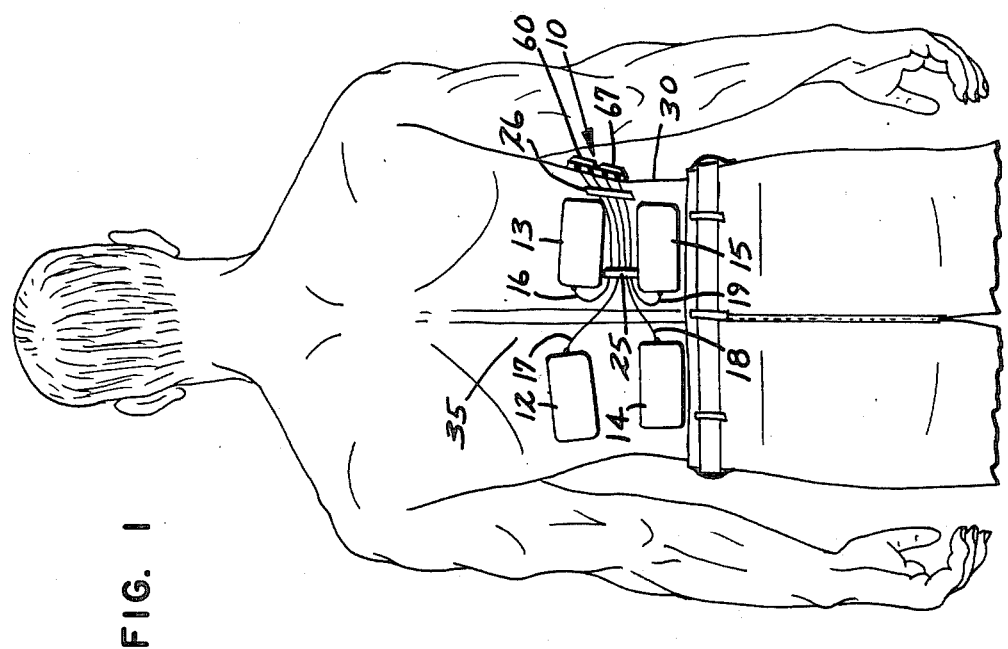
FIG. 2 shows a side view of the stimulus generator and electrodes attached to a human body.

FIG. 2 shows a side view of stimulus generator 10 attached to side area 30. Input jacks 31–34 are connected to the respecctive leads 16–19 which are in turn connected to their corresponding electrode on the patient's back 35. Input plugs 31-34 are inserted in plug receptacles recessed in generator 10 providing for ready replacement or interchangability of electrodes 12-15.

FIG. 3 shows a patient fully clothed and having electrodes 12-15, leads 16-19 and generator 10 fully concealed beneath shirt 36. Also shown is remote controller 37 being actuated by the patient for electronic remote control of generator 10 via electromagnetic or other coupling means. Indicator or display 38 provides operational mode information to the patient with controls 39 allowing for remote programming of generator 10. As illustrated, through-the-clothing wires or leads are eliminated. Display 38 may be in the nature of a liquid crystal display (LCD) or LED indicator lights. Full alpha-numeric message displaying capability could also be included, using scrolling or other alpha-numeric display techniques. Controls 39 may be a keypad, or one or more potentiometers and switches, or any combination thereof.

FIG. 4 is a functional block diagram of the electronics corresponding to remote controller 37 and stimulation generator 10 according to the present invention. Reference numeral 40 generally indicates the electronics associated with the controller 37 while reference numeral 41 generally indicates the electronics associated with generator 10. In operation, user input 42a is programmed by the patient, causing control signals to be communicated to remote control logic 42b for interpretation and formatting. These control signals include stimulation parameter or mode information such as stimulus frequency, stimulus intensity, on-off etc. Properly formatted, the control signals activate display 42c and receiver/transmitter 42d, indicating to the patient the programmed mode and causing the transmission of electromagnetic control signals to generator electronics 41.

Generator electronics 41 include a receiver/transmitter 43a which receives electromagnetic control signals 44 from transmitter 42d. The received signals are demodulated and passed to stimulation control logic 43b for interpretation or decoding and storage threin. Stimulation genertor 43c is responsive to control logic 43b, delivering to stimulation output terminals 43d the particular mode of stimulation selected via programmer 37. Stimulation generator 43c may also include a mechanically actuated "panic-off" switch whereby stimulus generation could be quickly stopped without recourse to the remote controller 37. Referring to FIGS. 5 and 9, off-switch 47 may be mounted in stimulation generator 10 so as to provide easy access to the patient while insuring against inadvertant actuation thereof by utilizing a slide switch as shown, or any other switch of suitable configuration. It is also contemplated that a similar off switch 45 be incorporated in the remote controller 37, preferably connected to or incorporated in user input electronics 42a illustrated in FIG. 4. It will be understood that the electronics of the present invention may be of digital design, analog design or a combustion of both.

FIGS. 5 and 6 show respective top and side views of generator 10 enclosed or potted in flexible housing 50, which may constitute any suitably flexible non-conductive material. Housing 50 comprises housing modules 60-67. Modules 61-66 each house a rigid printed circuit board as exemplified in FIG. 7 by reference numbers 73, 74, and 75. Modules 60 and 67 house receptacles 51-54. Rigid boards 73, 74, and 75, and the others not shown, have mounted thereon components 92 or batteries 91 which comprise the electronic elements necessary for the generation of electrical stimulus and the decoding of remotely generated control signals. It will be understood that batteries 91 may be removably mounted in the housing so as to provide for their replacement when necessary, or may be rechargeable via an appropriate external access.

As illustrated in FIG. 7, each module's corresponding circuit board is flexibly connected to the adjacent rigid board through flexible printed circuit board. Flexible boards 76 and 78 connect rigid board 73 to board 74, and to receptacles 53 and 54, respectively. Flexible board 77 connects rigid boards 74 and 75. Accordingly, generator 10 is flexible about its axes 80, 81, 82 and 83 (FIG. 5) providing for a comfortable conformance to the patient's side or to any other suitable body area for most normal activities.

In FIGS. 6 and 7 two-sided adhesive pad 90 is shown attached to the bottom of housing 50 so as to provide a disposable means for securing stimulation generator 10 to the patient. Pad 90 includes adhesive materiels 94 on either side thereof and a disposable backing 93, to be removed prior to attachment of generator 10 to the body. FIG. 6 further illustrates housing 50's flexibility along axes 81 and 82.

FIGS. 8 and 9 illustrate an alternative embodiment of the present invention in which electrodes 100 and 102 replace adhesive pad 90 so that electrical tissue stimulation may be provided underneath generator 10. Electrodes 100 and 102 connect to the generator electronics through receptacles 104 and 106 respectively. Receptacles 104 and 106 are shown in dotted lines in FIG. 8, with a sideview of receptacle 104 shown in FIG. 9. Also, in FIG. 9 there is shown electrode 100, which includes foil 110 for electrical connection to receptacle 104 and adhesive surface 112 for attaching stimulator 10 to thebody and for delivering electrical stimulation. It will be seen that receptacles 54 and 104 may be wired together so that either may be utilized, and that off-switch 47 is interposed between the receptacles and the stimulation electronics. As illustrated in FIG. 9, this embodiment provides for the placement of one electrode, for example electrode 100, on the underside of stimulator 10 with a complementary electrode 114 in a remote location. It will be seen from the foregoing that more than two underside receptacles may be provided if desired, for use with any number of remotely located electrodes.

The operation of the present invention will now be explained. Referring to FIGS. 1 and 2 stimulation generator 10 is adhesively attached to the side 30 of the patient. Electrodes 12-15 are adhesively attached to the skin over the desired area and connected via the corresponding leads 16-19 and plugs 31-34 to the corresponding outputs of generator 10. Referring to FIG. 3, the patient programs or controls generator 10 with remote controller 37, using inputs 39, while monitoring generator mode from display 38 and the physical sensations so that maximum tissue stimulation efficacy results. It will be understood that the electrodes may be attached to the body underneath the generator 10, as illustrated in FIGS. 8 and 9.

While actuated, generator 10 utilizes replaceable or rechargeable power source 91 contained in one or more of modules 61-66 to produce electrical tissue stimulation at electrodes 12-15. When the patient is satisfied with stimulation mode remote controller 37 may be deactivated and put away, for example in a pocket or purse, until a future change in stimulation mode is desired. Meanwhile, generator 10 operates indefinitely in the mode last programmed.

It will be seen from the foregoing that the present invention eliminates the need for awkward, bothersome and unavoidably conspicuous through-the-clothing wires. The result is an electrical tissue stimulating apparatus of improved appeal to those who have a choice between electrical tissue stimulation and other forms of therepy such as drugs, which may cause unpleasant or undesirable side effects not caused by electrical tissue stimulation.

What is claimed is:

1. A transcutaneous electrical tissue stimulator, comprising:
    a housing and means for positioning it in use between the body and the outer clothing;
    one or more transcutaneous electrodes for attachment to the skin, said electrodes including wire leads;
    stimulation generating circuit means for producing electrical stimulation and means for mounting it within said housing, said generating means electrically coupled to said electrodes through said leads;
    said stimulation generating circuit means including means for receiving remotely generated programming signals and altering one or more modes or parameters of said electrical stimulation in response to said programming signals ; and
    hand-sized remote control means including user actuated controls for generating and transmitting programming signals to be received by said receiving means to permit a user to control said stimulation generating circuit means from a position remote from the location of said housing.

2. An apparatus according to claim 1 wherein said housing includes means for adhesively attaching to the human body.

3. An apparatus according to claim 1 wherein said housing includes electrodes mounted on the underside thereof, said electrodes electrically connecting to said stimulation generating circuit means so that electrical tissue stimulation may be delivered to body tissue underneath said housing when the underside of said housing is positioned against the body.

4. An apparatus according to claim 1 wherein said means for mounting said stimulation generating circuit means comprises a plurality of circuit boards flexibly connected to provide a plurality of axes about which said means for mounting may bend to conform to the contours of the human body and wherein said housing is flexible at least along said axes of bending of said means for mounting.

5. An apparatus according to claim 4 wherein the electrical connections between said circuit boards comprise flexible printed circuit boards.

6. An apparatus according to claim 5 wherein said circuit boards and stimulation generating circuit means are potted in said housing.

7. An apparatus according to claim 1 wherein a power source is enclosed in said housing for powering said stimulation generating circuit means.

8. An apparatus according to claim 1 wherein said remote control means includes a keypad and LCD for entering and reviewing programmed information.

9. A transcutaneous electrical tissue stimulation device for use with transcutaneous electrodes having wire leads, comprising:
    a flexible housing and means for holding said housing in use on or adjacent a human body at least underneath the outer clothing;
    stimulation generating circuit means for producing electrical tissue stimulation;
    control circuit means connected for control of said generating circuit means in response to remotely generated control signals;
    means for mounting said generating and control circuit means within said housing and for electrically coupling said generating circuit means to the electrode leads, said means for mounting comprising a plurality of circuit board means for mounting the electrical components of said generating and control circuit means thereon and flexible circuit path means for electrically interconnecting the electrical components and mechancially connecting the circuit board means; and
    wireless user operable means for generating and transmitting control signals to be received by said control circuit means to permit the stimulation mode of said generating circuit means to be controlled from a location remote from said housing.

* * * * *

UNITED STATES PATENT AND TRADEMARK OFFICE
CERTIFICATE OF CORRECTION

PATENT NO. : 4,690,144

DATED : September 1, 1987

INVENTOR(S) : Mark T. Rise, et al.

It is certified that error appears in the above-identified patent and that said Letters Patent is hereby corrected as shown below:

Column 1, line 19 "ob" should be --of--.

Column 1, line 24 "this" should be --This--.

Column 1, line 64, "mde" should be --mode--.

Column 3, line 42 "threin" should be --therein--.

Column 3, line 43 "genertor" should be --generator--.

Column 4, line 22 "materiels" should be --materials--.

Column 4, line 38 "thebody" should be --the body--.

Signed and Sealed this

Nineteenth Day of January, 1988

Attest:

DONALD J. QUIGG

Attesting Officer

Commissioner of Patents and Trademarks